United States Patent [19]

Inamura et al.

[11] 4,455,609

[45] Jun. 19, 1984

[54] APPARATUS FOR REALTIME FAST RECONSTRUCTION AND DISPLAY OF DOSE DISTRIBUTION

[75] Inventors: Kiyonari Inamura; Yasuo Ueda; Nobumasa Furushima; Keisuke Shigaki, all of Tokyo, Japan

[73] Assignee: Nippon Electric Co., Ltd., Tokyo, Japan

[21] Appl. No.: 301,012

[22] Filed: Sep. 10, 1981

[30] Foreign Application Priority Data

Sep. 17, 1980 [JP] Japan ............... 55-129549

[51] Int. Cl.³ .............................................. G01T 1/16
[52] U.S. Cl. .................................. 364/414; 364/413; 364/518
[58] Field of Search ............... 364/413, 414, 415, 518, 364/525; 340/705

[56] References Cited

U.S. PATENT DOCUMENTS

| | | | |
|---|---|---|---|
| 3,871,579 | 3/1975 | Inamura | 364/413 X |
| 4,042,811 | 8/1977 | Brunnett et al. | 364/414 |
| 4,135,247 | 1/1979 | Gordon et al. | 364/414 |
| 4,202,037 | 5/1980 | Glaser et al. | 340/705 X |
| 4,259,721 | 3/1981 | Kuznia | 364/413 |

Primary Examiner—Errol A. Krass
Assistant Examiner—Kevin J. Teska
Attorney, Agent, or Firm—Blakely, Sokoloff, Taylor & Zafman

[57] ABSTRACT

Apparatus for realtime fast reconstruction and display of dose distribution which calculates the dose of absorbed radiation in an irradiated area defined by coordinates and displays the results of the calculation. The apparatus comprises an input unit capable of setting parameters in the form of time-continuous quantities; a dedicated digital computer serving to control the input by the input unit; and a dedicated fast reconstructer for calculating the absorbed dose for each coordinate in the exposed area at a high speed by decomposing calculation formulae necessary for obtaining isodose curves on the basis of the parameter set in the input unit and effecting parallel calculation of the decomposed formulae, thereby obtaining the isodose curves; and video display for storing and displaying the isodose curves classified in terms of different isodose levels. The calculation is normally cyclically repeated to provide a motion picture of the dose distribution when the magnitude of the parameters is varied.

3 Claims, 9 Drawing Figures

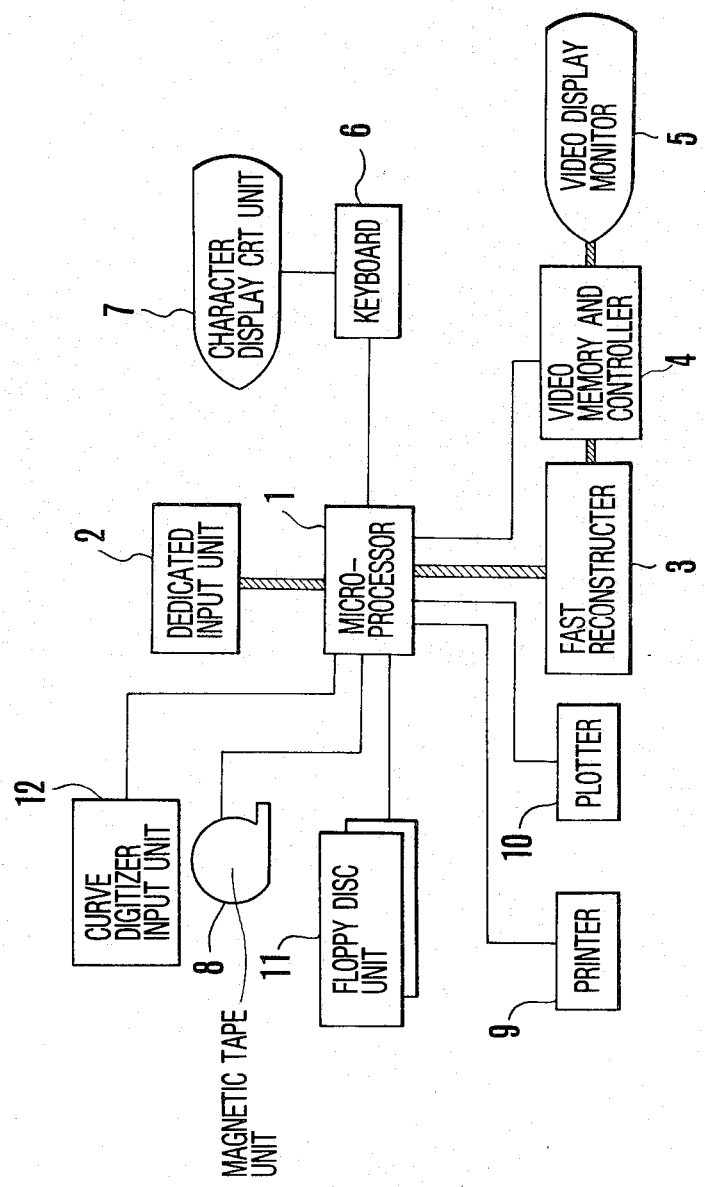

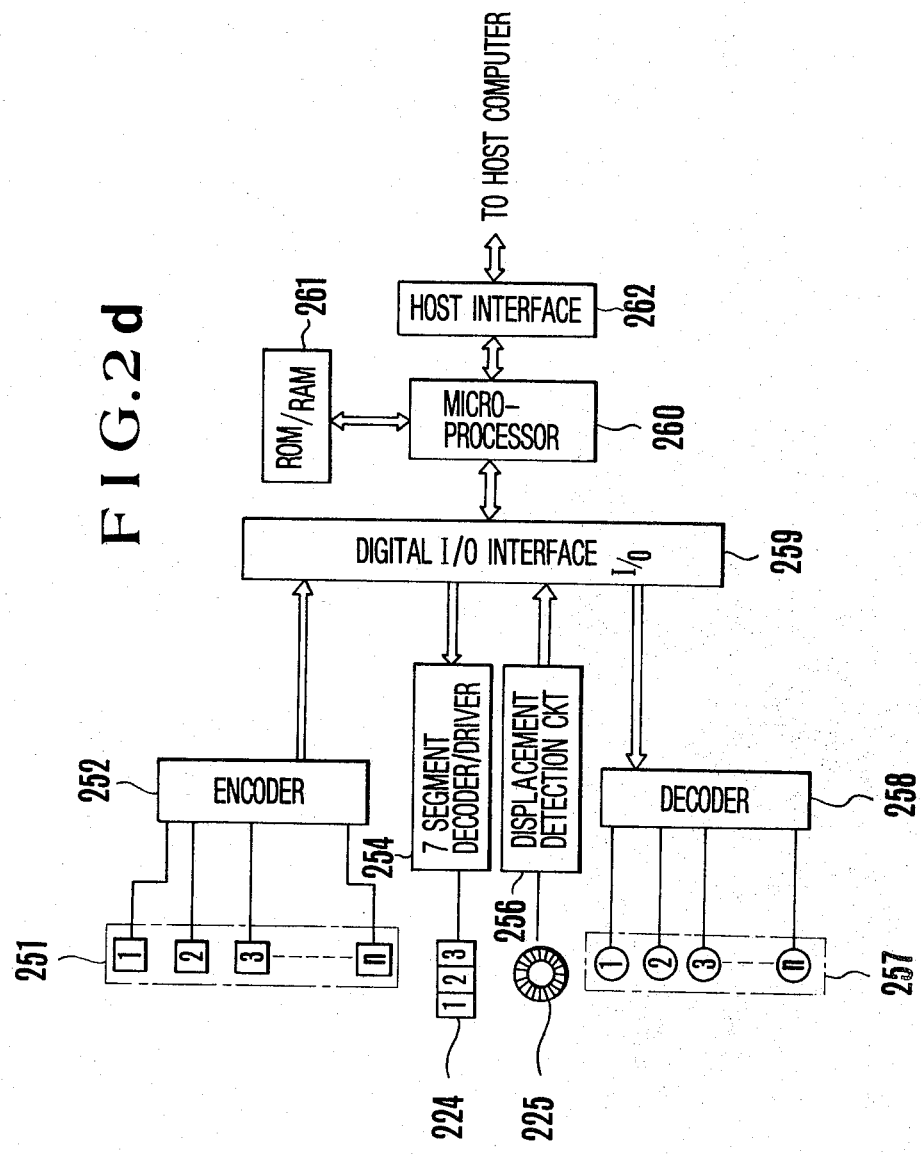

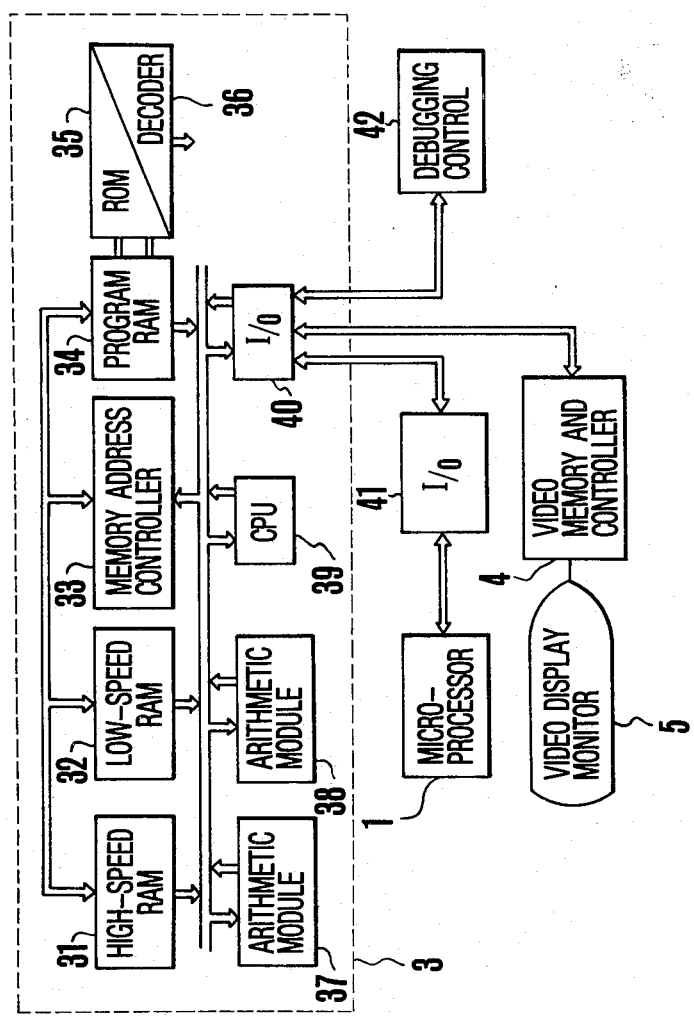
F I G. 3a

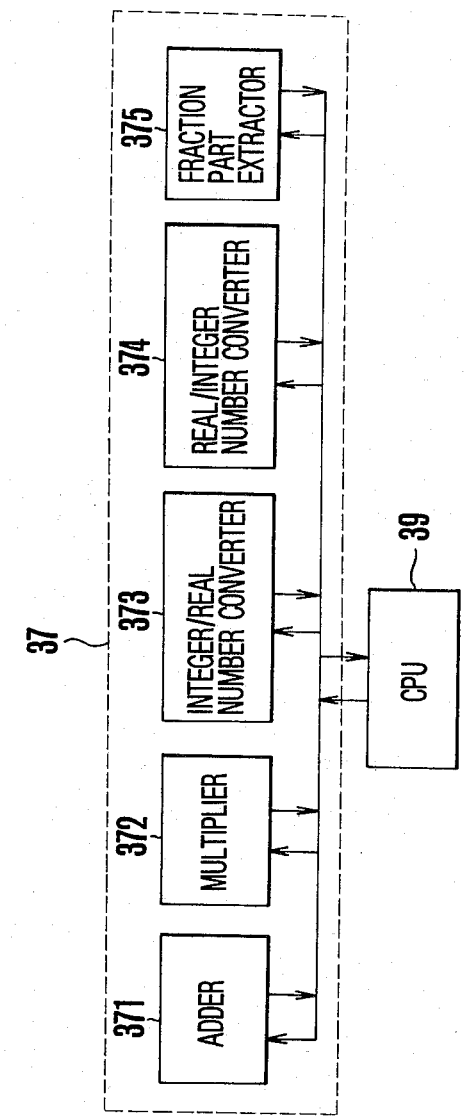

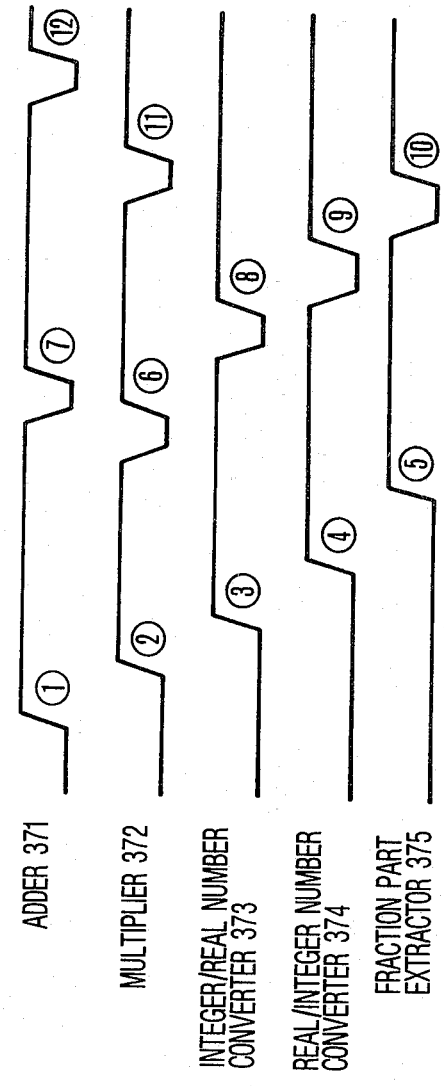

APPARATUS FOR REALTIME FAST RECONSTRUCTION AND DISPLAY OF DOSE DISTRIBUTION

BACKGROUND OF THE INVENTION

This invention relates to apparatus for realtime fast reconstruction and display of dose distribution, which is used for calculating the distribution in a patient's body of the absorbed dose of radiation, displaying the results of the calculation in the form of isodose curves, and determining the optimum conditions of radiation, thereby aiding in drawing an effective radiotherapeutic plan for the particular patient.

For radiotherapy, it is important that the radiation should be applied to a patient's body in such a manner that only a tumor and its immediate vicinity is allowed to absorb a required dose of radiation and the remaining healthy tissues are not caused to absorb any appreciable dose of radiation. For this purpose, various radiotherapeutic instruments are devised so as to provide a variety of radiation techniques adaptable by the operation of a host of parameters to thereby meet all conceivable positions and shapes of tumor to be treated. To this end, devices for the optimization (realtime fast reconstruction and display) of dose distribution are used. Such a device for realtime fast reconstruction and display of dosage distribution is disclosed in U.S. Pat. No. 3,871,579. Since this device is designed to determine an effective radiation technique by series calculations making full use of various parameters, the first round of calculation performed on the therapeutic condition takes up some time. Besides, the device requires a relatively long time period for optimization and therefor requires several rounds of such calculation. In addition, this device has disadvantages that it has no capacity for memorizing the optimum conditions concerning the parameters of all the therapeutic instruments involved and it is incapable of reflecting individual hospital policies undeterminable by realtime fast reconstruction and delicately variant rules of prescriptions observed by individual physicians. A variety of highly advanced therapeutic techniques have made appearance recently. Some of them call for far more fast reconstructions than have heretofore been used. Performance of so many fast reconstructions inevitably demands choice of preference between rapidity of reconstruction and accuracy of reconstruction. Thus, the device has inevitably to sacrifice one of the two preferences.

SUMMARY OF THE INVENTION

An object of this invention, therefore, is to provide an apparatus for realtime fast reconstruction and display of dose distribution. The apparatus is designed to operate on the principle of dividing calculation or reconstruction formulae, which are repeatedly used in the calculation of dose distribution, into groups of equal size components and parallelly performing calculations on these groups of equal size components, thereby decreasing the calculation time. Such design overcomes one of the faults found with the conventional device, enabling the parameters indispensable to the calculations to be changed as required from time to time in the course of calculations, and consequently changing the various parameter in analog form to optimize isodose curves by visual recognition of changes of isodose curves.

Another object of this invention is to provide apparatus for realtime fast reconstruction and display of dose distribution which enables optimum therapeutic conditions to be found by having dose distributions and isodose curves on one plane displayed at a rate of about 20 times per second, for example, namely in the form of a motion picture corresponding to continuously changing therapeutic parameters.

Yet another object of this invention is to provide apparatus for realtime fast reconstruction and display of dose distribution which utilizes the aforementioned capability of ultra-high speed arithmetic operation in materializing the logical optimization or mathematical optimization which permits automatic determination of therapeutic conditions and dose distribution optimized for anatomical structures of the human body of a given patient and for the position, shape, and size of the tumor.

A further object of this invention is to provide apparatus for realtime fast reconstruction and display of dose distribution which, by utilizing directly CT (computerized tomography) images reconstructed by a CT unit and stored in a magnetic disc or magnetic tape, retrieves the internal information of the body of a patient having a tumor, aiding in the aforementioned realtime fast optimization.

In the apparatus of this invention, when the therapist or equivalent professional engaging in radiotherapy feeds the apparatus with data concerning the patient under treatment and gives it instructions for proper operations, the apparatus performs the operations of input, decision, arithmetic operations, output, etc. in accordance with the program introduced to the computer in advance or automatically repeats these operations until there are produced therapeutic conditions optimum for the particular patient under treatment. Although the fundamental operation of the apparatus of this invention is similar in a sense to that of any ordinary computer by the use of software, the apparatus of this invention includes, as dedicated hardware of one sort, the fast reconstructer designed to perform calculations on dose distribution for the purpose of determining therapeutic conditions optimized for the individual patients undergoing the radiotherapy. The apparatus, therefore, controls the peripheral computer so as to bring this dedicated hardware in the repetitive arithmetic operations at a maximum efficiency. In this respect, the operation of the apparatus of this invention differs from the ordinary computer operation. In other words, the apparatus embraces operations of its own different from the operations obtainable with ordinary computers. It performs the operations that cannot be attained by substituting the apparatus with any ordinary computer.

BRIEF DESCRIPTION OF THE DRAWINGS

FIG. 1 is a block diagram illustrating the preferred embodiment of this invention.

FIG. 2d is a block diagram of the dedicated input unit.

FIG. 3a is a block diagram illustrating the internal structure of an example of a fast reconstructer denoted by reference numeral 3 in FIG. 1.

FIG. 3b is a block diagram of an arithmetic module shown in FIG. 3a.

FIG. 3c is a time chart showing the operation of the arithmetic module.

DESCRIPTION OF PREFERRED EMBODIMENTS

Figure 2A:
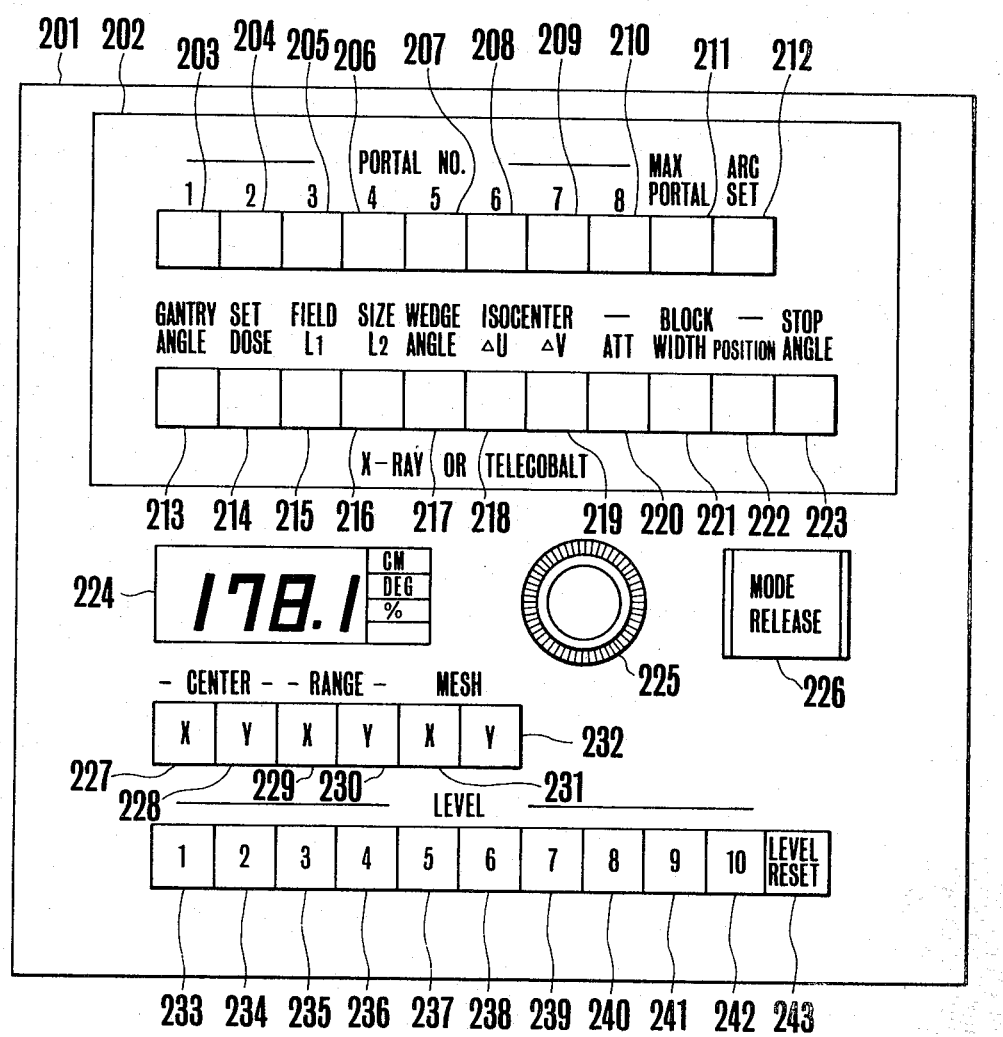
FIG. 2a shows an exemplary layout of an operation panel in a dedicated input device indicated by reference numeral 2 in FIG. 1, which operation panel is intended for application to the external radiation.

According to this invention, there is provided apparatus for realtime fast reconstruction and display (for instantaneous optimization) of dose distribution which comprises an on-line realtime combination of a unique, dedicated reconstructer capable of analyzing calculation formulae involved in dose calculation and performing a multiplicity of calculations parallelly, a dedicated parameter input board incorporating a freely adjustable potentiometer, and a dedicated digital computer adapted to control the parameter input board, whereby results of the reconstruction are converted into coordinate data groups of isodose curves within the dedicated reconstructer and further transferred to a video memory of a display video TV set to effect display of the isodose curves and, in the meantime, the reconstructions are repeated to follow changes in the input parameters to change the dose distribution for display on the display video TV screen, thus determining an optimum method of therapy.

When the apparatus of this invention is utilized for the therapy of the tumor in the body of a patient by the irradiation from an external source to the tumor, it permits determination of the optimum method of therapy by incorporation of an input device capable of freely changing, continuously in terms of time, therapeutic parameters and other parameters necessary for calculations. When the apparatus is utilized for the therapy of a similar tumor by the insertion or implant of a radiation source into the tumor or its vicinity within the body, it permits determination of the optimum method of therapy by incorporation of an input device capable of continuously and freely changing selected therapeutic parameters and other relevant parameters.

The apparatus of this invention is characterized by the fact that, owing to the automatic repetition of an operation which causes the parameter input board to issue information, the digital computer to convert this information from time to time into calculation parameters and transfer the produced data to the dedicated reconstructer, and the dedicated reconstructer to perform high-speed parallel calculation operation on the received data and from time to time display the results of the calculation operation in the form of isodose curves, the changes in parameters are reflected in isodose curves as by being immediately displayed on the CRT and the desired optimization is obtained simply and rapidly unlike the conventional device which requires the same handling of the machine to be repeated for trial and error calculations. Further by making the operating speed so high that the cycle involving the input of information to the parameter board, the high-speed parallel operations, and the display of the produced data can be repeated about 20 times within one second, the dose distribution can be displayed in the form of a motion picture corresponding to continuously changing therapeutic parameters and, consequently, the determination of the optimum therapeutic conditions can be further facilitated. From the clinical point of view, this apparatus enables the therapist to change therapeutic parameters by faithfully following the isodose curves displayed in the form of a motion picture and stop changing the parameters and bring the motion picture to a stop at the moment that he finds the dose distribution optimized for the patient under treatment, thus accomplishing desired optimization of the dose distribution in the patient.

Particularly when the operation of the apparatus provided by this invention is applied to the therapy by the use of a radiation source inserted or implanted into the tumor or its vicinity in the body of the patient, the optimization can be obtained by performing the high-speed operation just once on given therapeutic parameters and immediately displaying the results of the operation in the form of isodose curves. When a dedicated input unit capable of admitting, as its input, anatomical structure of the internal organs, contours, and tumors in the patient's body is incorporated in place of the aforementioned unit capable of continuously changing parameters necessary for the calculation of dose distribution and software and operating procedure of the apparatus of this invention are accordingly modified, the fast reconstructer can be utilized for materializing automatic calculation of dose distribution and therapeutic parameters which are optimized for the data on a given patient which had been admitted into the dedicated input unit.

When the apparatus of this invention additionally incorporates a magnetic tape unit, a magnetic disc unit, or some other similar memory medium input unit, along with additional software and correspondingly modified operating procedure, the apparatus can retrieve the CT image information stored in the memory medium such as the magnetic disc and display the CT image information on the image display included originally in the apparatus. Moreover, by direct use of the CT images, the apparatus can extract the body contour, determine the density distribution or the X-ray absorption coefficient distribution in the body, and reflect such information in the calculation of dose distribution. Thus, the apparatus of this invention can be made to possess functions and characteristics in combination with the whole or a desired part of the aforementioned characteristics.

FIG. 1 is a diagram illustrating the preferred embodiment of this invention. As illustrated, there is provided a micro-processor 1, a dedicated input unit 2 controlled by and connected to the micro-processor, a fast reconstructer 3 for the calculation of dose distribution, a video memory/controller 4, a video display monitor 5, an alphanumeric keyboard 6 adapted to accept instructions from the operator, a character display CRT unit 7 adapted to display the information introduced through a keyboard as well as the information issued from the central micro-processor 1, a magnetic tape unit 8 adapted to read data from a magnetic tape storing CT images, a printer 9 adapted to print out the results of arithmetic operation and the results of optimization in the form of alphanumeric data, a plotter 10 for producing figures, particularly, isodose curves, and a magnetic floppy disc unit 11 serving to read in programs for executing fundamental operations aimed at by the present invention, store information on patients, and read in stored information. Further, a curve digitizer 12 is connected to the micro-processor 1. It is used for admitting information on the body contour and anatomical structure of the patient as well as information on the positioning of radiation source inserted or implanted into the patient body.

Referring to FIG. 1, the information including the identification number, name and data of birth of the patient subjected to radiotherapy and other diagnostic data and treatment strategy is introduced into the microprocessor 1 in the form of alphanumeric and KANA data (i.e. Japanese characters) through the keyboard 6 and the character CRT display unit 7. The information is transferred to tne floppy disc 11 and stored therein as a patient file. When the therapy is effected by applying radiation from an external source into the tumor in the body of the patient, the information including the body contour, the position, shape, and size of the tumor, and other anatomical structure such as the contour of the lungs, the positions of bones and other internal organs of clinical significance is introduced through the curve digitizer 12. When the therapy is effected by the use of a radiation source inserted or implanted into the tumor or its vicinity in the body of the patient, the curve digitizer 12 is also utilized for the introduction of the information on the position of the radiation source photographed on a film.

The magnetic tape unit 8 reads out CT image data from the magnetic tape containing such CT images and delivers the data to the processor 1. The processor 1 processes the CT images received from the magnetic tape unit 8 and converts them into data similar to anatomical structure on the patient introduced through the curve digitizer 12. Namely, these data are used effectively for extraction of body contour, conversion of the CT number matrix to the density or X-ray absorption coefficient matrix, in order to correct imhomogenity of density during the calculation of dose distribution. The floppy disc unit 11 is required to make the processor 1 memorize therein programs of dose distribution calculations which depend on what type of therapeutic method is employed in the operation of the apparatus of this invention. Floppy discs are prepared one each for different kinds of programs, namely different kinds of therapeutic methods adopted. To introduce to the processor 1 a particular program conforming to one therapeutic method, the floppy disc unit 11 functions to store the patient file in the floppy disc or read out data from the floppy disc containing the CT image in much the same way as the magnetic tape unit 8. The printer 9 serves to tabulate all the character information necessary for effective use of the apparatus of this invention, including parameters of therapeutic conditions obtained by the calculation of dose distribution, individual diagnostic data on patients and other therapeutic data, and statistical data necessary for the registration of tumors. It also produces optimum therapeutic parameters existing after the completion of optimization.

The plotter 10 is used for depicting isodose curves representing the results of the arithmetic operation namely reconstruction or the results of optimization. In this case, the plotter 10 is capable of depicting the isodose curves with the anatomical structure of the patient superimposed thereon and introduced in advance through the curve digitizer 12, the magnetic tape unit 8, or the floppy disc unit 11.

Figure 2B:
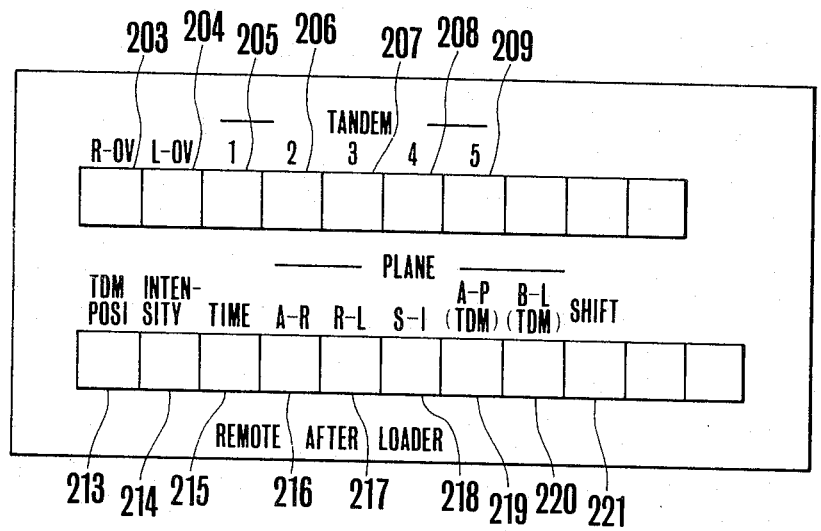
FIGS. 2b and 2c show modifications of a keyboard indicated by reference numeral 202 in FIG. 2a, which modifications are intended for application to the radiation by use of a radiation source inserted to the body of a patient and implanted within the tissue, respectively.
Figure 2C:
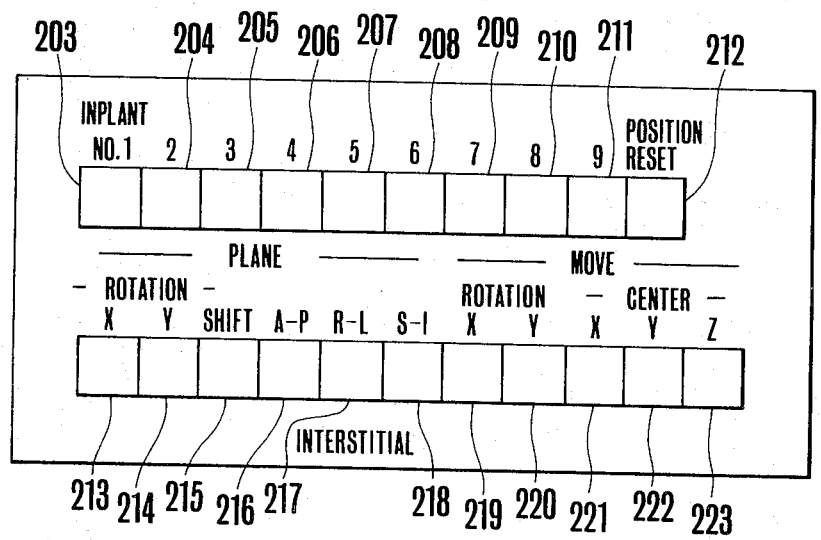

The dedicated input unit 2 constitutes itself one of the important elements for the construction of the present invention. A typical example of the dedicated input unit is illustrated in FIG. 2a. It will be described more fully hereinafter. When the operator continuously rotates the potentiometer, the dedicated input unit changes the therapeutic conditions continuously. It serves to forward to the processor 1 the therapuetic conditions which are changed at suitably short sampling intervals. In the illustrated embodiment, the particular therapeutic parameters desired to be changed can be selected by use of push-button switches 203-223. The dedicated input unit can be adapted to suit some other different therapeutic technique by changing the template as shown in FIGS. 2b and 2c and modifying the program accordingly. The fast reconstructer 3 is the most important of all the elements for the construction of this invention. It will be described in detail later with reference to FIG. 3a.

The video memory and controller 4 receives and rewrites the coordinate data of isodose curves representing the results of arithmetic operations from the aforementioned fast reconstructer 3 each time the calculation is completed and, in the meantime, transfers analog video signals at a rate of a predetermined number of frames per second to the video monitor 5, to effect display of isodose curves. Since the anatomical information such as the body contour of the patient which has been introduced through the aforementioned curve digitizer 12 is directly transferred from the processor 1 to the video memory and controller 4 and written therein, this information can be displayed as superposed on the isodose curves. Further, the CT image information introduced through the magnetic tape unit 8 or the floppy disc unit 11 is similarly transferred directly from the processor 1 to this video memory and controller 14 and displayed as superposed on the isodose curves. Since the CT images contain the gray scale, the video memory is also adapted to incorporate the gray scale.

Figure 4:
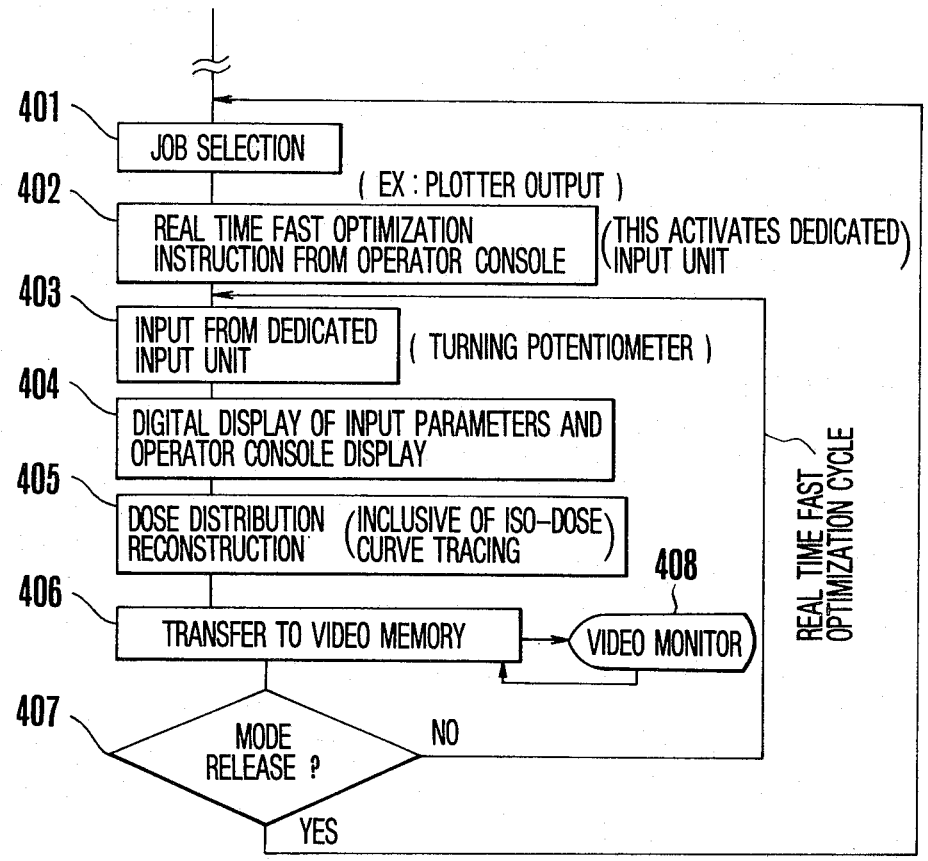
FIG. 4 is an operational flow chart for the operation of this invention.

The video monitor 5 displays the image which is received from the video memory/controller 4. This image represents the isodose curves produced by the calculation performed in the fast reconstructer, the isodose curves as superposed by the anatomical information of the patient introduce through the curve digitizer 12, or the isodose curves as superposed by the CT images. The realtime fast optimization contemplated by the present invention if effected by the configuration which comprises the dedicated input unit 2, the processor 1, the fast reconstructor 3, the video memory/controller 4 and the video monitor 5. A flow chart of this configuration is illustrated in FIG. 4. It is noted from the flow chart that the cycle involving the steps of inputting of information from the dedicated input unit, calculation of dose distribution, and display of the results of calculation is automatically repeated to effect the realtime fast optimization. When the numeral values of parameters are changed by continuously turning the knob of the dedicated input unit during the repetition of the cycle mentioned above, the isodose curves displayed appears like a motion picture.

The component elements for the construction of one preferred embodiment of this invention have been described with reference to a block diagram. Now, the dedicated input unit 2 and the fast reconstructer 3 which are important elements for the construction of this invention will be described below with reference to FIG. 2d and FIG. 3a respectively. Then, the present preferred embodiment will be described with reference to the schematic flow chart of FIG. 4. Thereafter, the manner in which the calculation of dose distribution is carried out will be described.

FIG. 2a, FIG. 2b and FIG. 2c represent the front panel of the dedication input unit 2. FIG. 2a represents a typical operation panel of the dedicated input unit which is required to the realtime fast optimization of dose distribution by use of this device when the therapy is effected by external application of X-rays from linear accelerators (Lineac) or gamma rays from cobalt teletherapy unit, electron beams from Lineac, X-rays or electron beams from Betatron, or fast neutron from Cyclotron to the tumor in the patient body. First, 201 denotes the front face of the operation panel. To ensure the operator's access, the operation panel is placed on a desk or installed upright. By 202 is denoted a template which is perforated at portions set apart for the pushbutton switches 203-223. The descriptions of utilization of these pushbutton switches 203-223 are inscribed along the edges opposite the respective switches. There are as many templates as therapeutic methods available. This template 202 indicated herein is intended for the aforementioned external beam irradiation. A dial 225 is used for continuously changing the therapeutic parameters designated by the pushbutton switches 203-223. By turning this dial, the numerical values to be introduced into the microprocessor 1 can be continuously changed. A numerical indicator 224 displays momently the numerical value of the parameter first designated by the pushbutton switches 203-223 and then changed by the rotation of the dial 225. As the denomination of the unit of parameters thus displayed, there may be used cm, degree, percent, etc. The data displayed in the numerical indicator 224 are the data being introduced momently to the micro-processor 1. The pushbuttons 203-210, when the external beam irradiation used for the therapy is given in the form of a multi-portal radiation, are for the purpose of designating the number of the portals involved and changing the therapeutic parameters of the designated portal number by means of the dial 225. In the illustrated embodiment, the pushbuttons 213-223 are adapted to designate the therapeutic parameters for desired portal numbers designated by the pushbuttons 203-210 and allow the parameters thus designated to be changed by the rotation of the dial 225. As regards the functions of the pushbuttons 213-223, the gantry angle (incident angle of radiation) for each portal is designated by 213, the preset dose of radiation for each portal by 214, the size of radiation field for each portal by 215 and 216, the wedge filter angle for each portal by 217, the coordinates of the position of isocenter in the patient body by 218 and 219, and the variables such as, for example, attenuation ratio, width, and position, at each portal when the block filter is used by 220, 211, and 222. Finally, when the rotation therapy is set by the pushbutton 212, the gantry stop angle can be designated by depressing the pushbutton 223. The pushbutton 211 is used for designating the number of portals where the radiation is carried out in the form of multi-portal radiation. The number of portals for the multi-portal radiation can be designated by first depressing this pushbutton 211 and then depressing desired ones of the pushbuttons 203-210. A typical use of the pushbuttons 203-223 and the dial 225 is as follows. The sequential depressions of the pushbuttons 205 and 215 have the effect of designating the one side of field size for the portal number 3. When the dial 225 is rotated at this time, the existing parameter (that field size) is continuously changed, and the continuously and momently changing value is displayed on the numerical indicator 224 and subsequently, introduced into the microprocessor 1. These pushbuttons 203-223 are so adapted that just one dial 225 will suffice for the effective operation of the apparatus. This arrangement is not critical but may admit of modification. In one possible modification, for example, there may be incorporated as many dials 225 as the parameters 213-223 so that the dials will correspond one each to the parameters 213-223 to permit direct change of the input data. In another possible modification, there may be incorporated dials corresponding to the parameters 213-223, one each with respect to the pushbuttons 203-210. In this case, therefore, the number of dials totals 88 (8×11). The increasing number of dials results in increasing time required for the introduction of data to the micro-processor 1 because the number of the analog-digital converters increases with the increasing number of dials. From the standpoint of the operational speed, therefore, it is advantageous to adopt the method which, as illustrated in FIG. 2a, designates the portal numbers and the corresponding parameters by the plurality of pushbuttons and effects desired change of the parameters by means of just one dial 225. In the method which involves use of a multiplicity of dials, there is a possibility that the operator's hand busy at one dial will accidentally touch on other adjacent dials and cause unwanted changes in the numerical value of parameter. Impossibility of this accident constitutes one advantage of the method using just one dial.

The pushbuttons 227 and 228 serve to designate the coordinates of the center of the area on the cross-section of the patient body which is actually subjected to the calculation of dose distribution. The pushbuttons 229 and 230 are used for designating the range, that is, the longitudinal and lateral lengths of the area subjected to the calculation. The pushbuttons 231 and 232 are for designating the fineness of the meshes subjected to the calculation. The pushbuttons 233-242 are used for designating the levels of isodose curves when the results of the calculation of dose distribution are displayed. For example, they may be set so that 233 will designate 100%, 234 90%, . . . and 242 10%. The pushbuttons 229-242 are adapted so that when any of these pushbuttons is depressed, the numerical value of the parameter of that pushbutton is rendered changeable by the dial 225. The continuously changing data are successively introduced in the micro-processor 1 and, at the same time, similarly displayed momently on the numerical indicator 224. The pushbutton 243 is used when the level of the isodose curves already set is desired to be reset. The pushbutton 226 plays its part when the continuation of the routine cycle starting with the introduction of data to the processor 1 through the exclusive input device 2 is to be terminated. The therapist operates the exclusive input device 2 and keeps an eye on the CRT display 5 which displays the results of the calculation of dose distribution. At the moment that he finds the optimum dose distribution for the particular patient now under his attention, he stops rotating the dial 225. Consequently, the isodose curves displayed at that moment on the CRT display 5 freeze. He has at once to depress this pushbutton 226, so that all the therapeutic parameters frozen on the dedicated input unit 2 which have been in operation are tabulated on the printer 9 of FIG. 1 and, at the same time, the isodose curves are drawn out on the plotter 10. Optionally, the isodose curves may be photographed by the multi-format video camera which is connected to CRT 5. The pushbutton 226 is a switch for effecting an interrupt in the processor 1 to reset the apparatus for a new process by terminating the cyclic operation of the series of steps of transferring the data from the dedicated input unit 2 to the processor 1, performing the calculation of dose distribution in the fast reconstructer 3, and displaying the results of the calculation on the CRT display 5. The function of this pushbutton 226 will be touched upon in the description of the schematic flow chart of FIG. 4.

FIG. 2b represents a typical example of another template which may be used in place of the template 202 in the operation panel of FIG. 2a. It is used for assigning different significances to the pushbuttons 203–223 from those indicated in FIG. 2a. In the template of FIG. 2a, the pushbuttons 203–223 are intended for the selection of therapeutic parameters in the therapy by the external beam irradiation. In contrast, in the template of FIG. 2b, the same pushbuttons are designed to permit selection of therapeutic parameters for the therapy by the intracavitary irradiation. Referring to FIG. 2b, 203 represents a righthand ovoid radiation source, 204 a lefthand ovoid ratiation source, and 205–209 each number of stop position of the radiation source caused to override in the respective tandem applicator. The pushbutton 213 designates the position of the tandem radiation source at any of the position numbers 205–209 corresponding to the stop position number, 214 the intensity of the radiation source selected by 203–209, and 215 the exposure time by the relevant radiation source selected by 203–209. The pushbuttons 216–221 are used for causing the dial 225 to select the mode of continuous change of the cross section for the calculation of dose distribution, between the mode of translational movement and that of rotational movement; 216 representing the anterior-posterior plane of the body, 217 the right-left plane of the body, 218 the superior-inferior plane of the body, 219 the anterior-posterior plane of the body including the tandem, 220 the right-left plane of the body including the tandem, and 221 the amount of shift. For example, when the pushbuttons 206 and 215 are depressed in the order mentioned, the numerical value of the exposure time at the second of the tandem radiation sources can be changed by the dial 225. When the pushbutton 219 is depressed, the coronal plane including the tandem can be translated by rotating the dial 225. By continuously moving the cross section of the patient body subjected to calculation and display by use of the functions mentioned above, therefore, any delicate change or sudden change in the isodose curves can be observed without any oversight and the determination of the optimum therapeutic conditions can be facilitated.

FIG. 2c represents another example of a template which, by the expansion of the concept described in FIG. 2b, is made applicable to the therapy for tissues involving the internal radiation by use of a radiation source implanted into the patient body. To be specific, 203–211 designate the ratiation source numbers such as radium needles implanted into the patient body and 212 serves to reset the function of determining which number of radiation source has been designated. The pushbuttons 213–223 are used for designating the planes and points in which the translational or rotational movement of the cross section of the patient body subjected to calculation is to be effected continuously by the rotation of the dial 225. Examples of radiation sources which are effectively usable in the therapeutic method illustrated in FIG. 2b or FIG. 2c are grains and needle tubes of cobalt, cesium, iridium, and radium. The modifications due to the changes among these radiation sources can be materialized by suitably replacing the numerical values of parameters included in the calculation program which will be described later more fully. The tyical examples of FIG. 2b and FIG. 2c are not limited by the type of radiation sources to be used. The example of FIG. 2a can also be applied to all form of external radiation. It is not restricted by the type of radiation devices to be used. Thus, it can be applied to such therapeutic radiation devices as Liniac, cobalt, Betatron, and Cyclotron. If therapeutic devices or radiation sources are developed in the future which make the application of the appartus of this invention difficult in some respect or other, the difficulty can be easily eliminated by changing the designations of parameters representing the therapeutic conditions to be instructed to the pushbutton switches and slightly modifying the significances or denominations of the parameters included in the program as involved in the expansion of concept from FIG. 2a to FIG. 2b or FIG. 2c.

FIG. 2d represents a circuit diagram of the dedicated input unit. In the Figure, 251 denotes a group of pushbutton switches to be used for designating therapeutic parameters, portal numbers, and calculation parameters. These pushbuttons correspond to the pushbuttons 203–223 and 226–243 indicated in FIGS. 2a, 2b and 2c. By 252 is denoted an encoder adapted to receive the output from the group of switches 251 and produce data indicative of the particular pushbutton now in a depressed state. By 224 is denoted a numerical indicator adapted to display the numerical value of data received concerning the parameters selected in advance. Denoted by 254 is a 7-segment decoder/driver which serves for the numerical indicator 224. And 255 which also appears in FIG. 2a denotes a dial to be used by the operator for inputting the amount of displacement and 256 denotes a displacement detection circuit. The displacement detection circuit include an incremental rotary encoder interlocked with the rotation of the dial 225 and a counter for counting the output pulse train issuing from the encoder. Then, 257 denotes a group of lamps corresponding to the individual pushbuttons of the group 251, 258 denotes a decoder for selectively turning on the lamps of the group 257 in accordance with incoming data, and 259 denotes a digital interface for connecting the encoder 252, the 7-segment decoder/driver 254, the displacement detection circuit 256 and the decoder 258 to the micro-processor 260. The micro-processor 260 is responsible for the control and management of the exclusive input device. By 261 is denoted a memory for storing the control program for the micro-processor 260 and the work data currently under processing. It comprises ROM and RAM. Denoted by 262 is an interface between the micro-processor 260 and the micro-processor (host computer) (FIG. 1).

The present embodiment represents a case wherein the main control is entrusted to the host computer 1. Optionally, the burden may be wholly imposed on the dedicated input unit. In the present embodiment, when one of the parameter pushbuttons 251 is selected and depressed, that pushbutton number is converted to a code by the encoder 252 and the produced code is forwarded through the digital interface 259 to the micro-processor 260 and further delivered via the interface 262 to the host computer. The host computer 1 recognizes from the pushbutton number the parameter name demanded by the operator and then forward via the interface 262 to the micro-processor 260 the instructions to turn on the lamp corresponding to the pushbutton and turn off the lamp no longer necessary. Subsequently, the instruction from the micro-processor 260 is forwarded via the digital interface 259 to drive the decoder 258 and flicker the relevant lamp in the group of lamps 257. This is an answer to the parameter indication by the operator.

Subsequently, the host computer 1 issues the initial value immediately preceding the designated parameter and feeds this value via the interface 262 to the micro-processor 260. Then, the instruction from the micro-processor 260 is forwarded via the digital interface 259 to drive the segment decoder/driver 254 and display in the numerical indicator 224 the designated parameter data.

Then, the host computer, now awaiting the arrival of input data from the operator, issues via the interface 262 to the micro-processor 260 an instruction demanding supply of data on the displacement. The micro-processor 260 continues to monitor the movement of the dial 225 at the timing of its own through the medium of the displacement detection circuit 256. On receiving an interrogation from the host computer 1, the micro-processor 260 immediately responds to the interrogation by forwarding a data on a current displacement via the interface 262 to the host computer 1.

The host computer 1 adds/subtracts the displacement received from the micro-processor 260 in response to its own interrogation to/from the immediately preceding data (initial value in the first instance) and preserves the result. This result is also forwarded via the interface 262 to the micro-processor 260.

The micro-processor 260 transmits this value via the digital interface 259 to the segment decoder/driver 254, which decodes this value and turns on the numerical indicator 224. Until the operator selects the next parameter button, the cycle of the reception of the displacement data, addition/subtraction of the value of the data to/from the immediately preceding data, and display of the result of the calculation in the numerical indicator is repeated.

As described above, each time the host computer (micro-processor 1) requests the dedicated input unit 2 to feed input data at a frequency of several to several of tens of times per second, new data corresponding to the movement of the dial 225 are fed into the host computer. The timing of the request for data input is settled at a block 403 termed "input from the dedicated input unit" in the realtime fast optimization cycle indicated in the flow chart of FIG. 4, and it is governed by the execution of the program in the host computer 1.

FIG. 3a illustrates one example of the fast reconstructer which constitutes itself the most important of all the elements for the construction of the present invention. The illustrated configuration is aimed solely at enabling the dose distribution to be calculated at an extremely high speed. It is quite unlike the mere general-purpose array processor which is aimed at performing subsidiary arithmetic operations on behalf of the host computer. The fast reconstructer is featured by the form of module of a series of processing methods. This fast reconstructer may well be compared to a sort of black box. When the anatomical data such as the patient's body contour and the therapeutic parameters are fed to this black box, the isodose curves as the results of calculation are displayed. These isodose curves are expressed by a planar 256×256 matrix and issued in the form of digital values. These digital values are stored in the video memory. By the video memory and controller, the relevant data are displayed in the video monitor. To enhance the adaptability of the dose distribution calculation for the radiation technique, or to render the calculation of dose distribution adaptable for the external radiation involving the application of radiation from an external source to the lesion within the patient body or for the intracavitary radiation or interstitial irradiation involving the insertion or implant of a radiation source into the tumor or its vicinity within the patient body, the internal structure of the fast reconstructer is designed so as to be controlled by software. To be specific, this device is adapted so as to function as firmware during its operation and it is composed of fine calculation modules so as to be adaptable to algorithms for a plurality of dose calculations. The process of the arithmetic operations is controlled by the micro-programs incorporated within the fast reconstructer itself.

Referring to FIG. 3a, 3 denotes the fast reconstructer and 31 through 40 denote the component elements used in this device; 31 standing for a high-speed RAM, 32 for a low-speed RAM, 33 for a memory address controller, 34 for RAM and ROM for storage of programs, 35 for a program sequencer, 36 for a program decoder, 37 for a floating decimal arithmetic module FPU, 38 for a function arithmetic module, 39 for a central processing unit CPU incorporated in the fast reconstructer, 40 for an input/output interface I/O between the fast reconstructer and the external devices, 1 for a micro-processor also indicated in FIG. 1. This micro-processor 1 constitutes a host computer relative to the fast reconstructer 3. Then, 41 stands for a parallel interface between the micro-processor 1 and the fast reconstructer, 4 for a video memory and controller (also indicated in FIG. 1), 5 for a video monitor (also indicated in FIG. 1), and 42 for a debugging console, which is used as part of the developing tool for micro-programs and is not used any longer after completion of micro-programs. The separation of RAM into a high-speed RAM 31 and a low-speed RAM 32 is aimed at lowering the cost, economizing the power consumption, minimizing heat dissipation, and elevating the real unit efficiency. The data demanding heavy, frequency accesses rely on the high-speed RAM 31, while data demanding no such access but necessitating large data areas rely on the low-speed RAM 32. For example, in the case of the external radiation involving application of radiation from an external source to the tumor within the patient body, the table of TAR (tissue air ratio), that of OCR (off-center ratio), that for the correction for the difference in the density in the body, etc. are allotted to the high-speed RAM 31, whereas the results of the calculation of dose distribution on a 64×64 matrix are allotted at a rate of six frames (6 planes) to the low-speed RAM 32. Besides, the anatomical structure of the patient is deposited to the low-speed RAM 32. The capacity of the high-speed RAM 31 is 4K words, while that of the low-speed RAM 32 is 128K bytes. Depending on the mode of application of the radiation subjected to the calculation, the whole capacity of 128K bytes is not required to be used up. Thus, the low-speed RAM 32 has tolerance in its capacity. The access time of the high-speed RAM 31 is 120 ns and that of the low-speed RAOM 32 is 720 ns.

FPU (floating point arithmetic module) 37 is designed to handle 20 bits of floating point numbers and 16 bits of fixed point numbers and perform the following arithmetic operations: the conversion of fixed point data to floating point data or vice-versa, the expression of data below decimal points in the form of floating points, and the multiplications, additions, and subtractions as arithmetic operations of floating points. The operation time is 240 ns for the conversion of floating points to fixed points and vice versa and 480 ns for the multiplications, additions, and subtractions of floating points. FXU (function arithmetic module) 38 takes the form of module for arithmetic operations required for interpolation of data often found necessary during the calculation of dose distribution. It possesses the arithmetic functions of $1/x$, $x$, $\sin x$, $\exp x$, $\log x$, $\tan x$, and $\tan^{-1} x$. The execution time is 360 ns. The modules of the aforementioned high-speed RAM 31, low-speed RAM 32, FPU (floating point arithmetic module), FXU (function arithmetic module) 38, etc. operate with a clock of 25 MHz. In this case, the fetch time for instructions is 120 ns and the decode time for instructions is 120 ns. The instruction execution time, therefore, is the sum of the aforementioned execution times for the individual modules and the fetch time and the decoder time. It is provided, however, that the instruction execution time for such a continuous operation as involved in the writing of data 10 times in the high-speed RAM is fixed not at $(120 \text{ ns} + 240 \text{ ns}) \times 10$ (here, 240 ns is the write time for the high-speed RAM) but at $120 \text{ ns} \times 10 + 240 \text{ ns} = 1440$ ns because the flying motion is rendered possible.

For the fast reconstructer to execute the calculation of dose distribution, micro-programs must be produced by using micro codes of the high-speed arithmetic operations. The algorithm of the calculation of dose distribution will be described later by way of example. For the production of micro-programs, the cross assembler resorting to a large computer is utilized as the tool of development. The micro-codes assembled here are written in the magnetic tape. The data thus stored in the magnetic tape are read by the micro-processor 1, one of the component elements of the apparatus of this invention (which corresponds to a host computer relative to the fast reconstructer 3) and, at the same time, stored in a memory medium such as the floppy disc 11. Whenever they are found necessary, they will be retrieved from such storage devices. In the program storage ROM 34 incorporated in the fast reconstructer 3, the wakeup program required for starting the fast reconstructer and the control program for the debug console 42 are stored in advance. When the debug console is connected to the program storage ROM 34, the control routine of the debug console is automatically started. The debug console 42 is necessary for debugging micro-programs and is capable of executing the operations of RUN, HALT, and 1 CYCLE of the fast reconstructer, displaying the content of the memories RAM and ROM, and writing data in the memories. The debug console 42 becomes no longer useful after the micro-programs for the calculation of dose distribution have been completed and the status of debug has been relieved. Thus, it may be excluded from the component elements indispensable for the configuration of the present invention.

The fast reconstructer, in its normal state having the debug console disconnected therefrom, awaits instructions from its host computer, i.e., the micro-processor 1. In other words, it is in the mode for reading data from the host computer. Between them an interposed parallel input/output lines of 16 bits and a simple control line for effecting input and output of data for such input/output lines. All these lines are connected to the fast reconstructer 3 and the micro-processor 1. Specifically, the input/output interface 41 which connects I/O 40 and the host computer 1 (micro-processor 1) to each other in FIG. 3a corresponds to such lines. For external control of the fast reconstructer 3, control commands are incorporated in a fixed sequence in the 16-bit data train. At the time of power source connection, the fast reconstructer 3 hoists a flag signaling the host computer 1 to make data input through I/O 41. The host computer, on recognizing this flag, transfers to the fast reconstructer 3 data transfer word number, head address stored in the program RAM of the fast reconstructer, start address, calculation program, table of constants (such as TAR, OCR mentioned above) necessary for calculation, and therapeutic parameters and calculation parameters designated by the dedicated input unit 2. Immediately the fast reconstructer 3 executes the aforementioned wakeup program, stores the incoming data in the stated addresses of the program RAM 34, and starts the calculation program from the designated address. On completion of a series of calculations, the fast reconstructer 3 again hoists a flag for demanding the host computer 1 to make data input and awaits arrival of input data. If, at this point, any one of the therapeutic parameters and calculation parameters designated by the dedicated input unit 2 has been altered, the host computer 1 transfers to the fast reconstructer 3 the data including the address storing the therapeutic parameters, the therapeutic parameters and the transfer word number, and the start address. Each time the series of calculations such as the calculation of dose distribution and the delivery of isodose curves to the video memory 4 are completed, the fast reconstructer 3 hoists a flag for demanding the host computer 1 to make data input. In this manner, the calculation of dose distribution is automatically repeated. The rate of the movement of isodose curves to be displayed on CRT 5 increases in proportion as the speed of the series of calculations increases. When the micro-programs in the fast reconstructer 3 are started to commence the calculation of dose distribution, the results of such calculations and successively stored in the low-speed RAM 32 as $64 \times 64$ matrix representing the cross section subjected to the calculations. For example, in the scratch pad area of RAM 32, the dose value resulting from totalling the dose values of the plurality of portals as involved in the aforementioned multi-portal external beam irradiation is stored. In the case of the internal radiation, the dose value of the total of the plurality of radiation sources against the serial numbers of the ovoid radiation sources and tandem radiation sources is stored. In the case of the radiation within the tissue, the value of the total of the plurality of radium needles and other radiation sources is stored. The results of the calculations on the $64 \times 64$ matrix are transferred to the high-speed RAM 31 at a rate of two lines, for example, at a time in the direction of the raster of the video display monitor. In the high-speed RAM 31, isodose curves are extracted from the incoming results of calculations by the interpolation technique and are successively transferred to the video memory 4. The transfer is effected in the form of busy/ready type handshake, with the isodose curves compressed to a 16-bit scale. Since the fast reconstructer 3 operates with micro-programs as described above, it can be made usable for general purposes, without departing from constraints on its own hardware, by suitable modification of such micro-programs. By the expression "general purposes" as used herein is meant the adaptability to all therapeutic methods described above and to the calculation of dose distribution on radiation therapy instruments.

FIG. 4 is a flow chart illustrating a typical time-course execution of the realtime fast optimization contemplated by this invention. As shown in the Figure, the operator with the aid of the job selection 401 selects the realtime fast optimization or other jobs such as, for example, issuance of the results of realtime fast optimization to the plotter or tabulation of therapeutic conditions on the printer. When the operator selects the realtime fast optimization, the instruction 402 causes the operator console (composed of the components 6 and 7 in FIG. 1) to issue an instruction to commence the realtime fast optimization. Consequently, an on-line connection is substantially established between the dedicated input unit 2 and the micro-processor 1. Then, by the input 403, the numerical values of parameters representing therapeutic conditions and calculation conditions are fed to the micro-processor 1. At the same time, these numerical values are digitally displayed in the numerical indicator 224 incorporated in the exclusive input device as shown in block 404. The same numerical values are also displayed on the operator console, specifically on the character CRT display unit 7. This operation of 404 proceeds almost simultaneously with that of 403.

Then follows the operation of the high-speed calculation 405. To be specific, the fast reconstructer 3 performs the calculation of dose distribution on the basis of the parameters of therapeutic conditions and calculation conditions brought in via the host computer from the dedicated input unit 2 as described above. It also executes the tracing of isodose curves as described above. When this operation is completed, the isodose curves are transferred to the video memory 4 in block 406 for transfer. The contents of the video memory are repeatedly displayed on the video display monitor 5 similarly to any ordinary TV monitor. As soon as isodose curves are newly written in the video memory 4, the isodose curves displayed on the video display monitor 5 are updated by the freshly received isodose curves. The repetition of the blocks 406–408 proceeds independently of the shift from block 406 to block 407. The operation of 407 which follows the operation of 406 is aimed at confirming whether or not the pushbutton 226 in the dedicated input unit 2 has been depressed as required. When the optimum dose distribution has been determined for the patient under treatment, the operation is returned to the step of 401 by the depression of the pushbutton 226, with the result that the optimum dose distribution is delivered to the plotter or the corresponding parameters of therapeutic conditions are printed out on the printer. When the optimum therapeutic conditions are not found, namely, before the optimum conditions have been found in the dose distribution displayed on the video display monitor 5, the pushbutton 226 remains undepressed. Thus, the step 403 is automatically initiated. Then, the operation of the steps 403–407, 403–407 . . . is cyclically repeated. This repetitive cycle will be referred to hereinafter as the realtime fast optimization cycle.

The present embodiment is based on the calculation formula described below. Let d stand for the depth of point on the beam axis from the skin surface and A for the field size of radiation, and the dose D (d, A) at the point will be found as follows:

$$D(d, A) = D_0 \cdot F_A(A) \cdot \left(\frac{SAD}{SSD + d}\right)^2 \cdot TPR(d', A) \times \quad (1)$$

$$OCR(d, T) \cdot W(\alpha_0, d) \cdot B(t,p,w)$$

wherein,
$F_A(A)$—field size coefficient for the field size A,
SAD—source-axis distance,
SSD—source-surface distance,
$TPR(d',A)$—tissue-peak ratio for d' (distance from skin surface) and A (field size),
d—distance from the skin surface at the foot of the perpendicular line drawn from the point of calculation to the beam axis,
d'—distance from the skin surface at the point of calculation,
$OCR(d, T)$—off-center ratio at the lateral distance T and at the distance of point d on the beam axis from the skin surface,
T—lateral distance of point of calculation from the beam axis,
$W(\alpha_0, d)$—correction coefficient for wedge filter where the wedge angle is $\alpha_0$ and the depth is d,
$B(t, p, w)$—absorption coefficient of the block filter, where t, p, and w represent parameters indicating attenuation ratio, position, and width.

The data for F(A), TPR(d', A) and OCR (d, T) are tabulated in advance. Where necessary, reference is made to the tables.

The correction coefficient for the wedge filter is determined by the following mathematical model.

$$W(\alpha_0 d) = W_F \exp(\alpha \tan \alpha \cdot x)$$

In the formula given above, $W_F$ denotes the attenuation ratio by the wedge on the beam center axis, $\alpha$ the empirical constant, and x the distance from the beam center axis. As the function of the depth d, the wedge angle is expressed as follows:

$$\alpha = \alpha_0 + [A \exp(B\alpha_0) + C][\exp(-Dd) - E]$$

In the formula, A, B, C, D, and E are constants obtained through experiments. They are to be determined for each specified energy of X-rays. The correction coefficient B (t, p, w) for the block is fixed by the following rule. $B(t, p, w) = t$ is satisfied when the point of calculation falls within the range of the position p and the width w of the block. Otherwise, $B(t, p, w) = 1$ is satisfied.

Now, the manner in which the calculation formula described above is reflected in the operation of the fast reconstructer 3 will be described. F(A) table, TPR table, and OCR table are stored in advance in the high-speed RAM 31. The anatomical data on the patient are stored in the low-speed RAM 32.

First, the initial value of the coordinates of the point of calculation is placed in the high-speed RAM 31. Then, the coordinates are converted into the (X, Y) coordinates system having the beam center axis as Y axis. Thus, the depths d and d' are easily calculated. Similarly, the parameter T and the field size A are calculated. By using the values thus found F(A) table, TPR table, and OCR table in the high-speed RAM 31 are referred to. These values are multiplied by using the arithmetic module 37 and the products are stored in the high-speed RAM 31. The values thus stored will be referred to as WORK. Then, the length of SSD is found and the value of $[SAD/(SSD+d)]^2$ is calculated with the aid of the arithmetic module 37. This value is multiplied by the WORK, with the product again stored in WORK. Further, the wedge correction coefficient and the block correction coefficient are found based on the aforementioned formula, and they are multiplied by the WORK. The value thus found represents the dose at the point of calculation. The loop described above is repeated for each of the points of calculation. The results of the calculation of dose are stored in a tabulated form in the low-speed RAM 32.

When this loop is completed, the group of coordinates of isodose curves are traced with the aid of the arithmetic modules 37 and 38. When this tracing is completed in one plane, the results are transferred to the video memory controller 41.

FIG. 3b illustrates, in block form, details of the interior of the arithmetic module 37 shown in FIG. 3a. To increase the operational speed, the individual modules 371 to 375 are operated independently. They are operated parallelly to preclude possible loss of time. The manner of their operation is depicted by the time chart of FIG. 3c. In FIG. 3c, ①, ②, ③ . . . indicate the sequence of the execution of the commands from the CPU 39. The modules 371 to 375 are programmed so that they are operated incessantly by the commands from CPU 39 and as large a number of them as possible are in operation without fail at any given point of time.

This invention involves a variety of expedients which are aimed at increasing the operation speed as described above. Some of these expedients concern the selection of sequence of calculation for the purpose of minimizing memory capacities to be occupied and increasing the calculation speeds. This invention is characterized by the fact that virtually all the calculation formats can be executed provided that they are simply converted into computer programs. Thus, from the methods of calculation already known in the art, typical examples adaptable to the optimization contemplated by this invention will be selected and described below. Other methods of calculation than the typical examples cited here can be executed by this invention so far as they do not differ fundamentally. Their effective application to this invention is accomplished by converting the methods of calculation into computer programs and then executing the programs by the method described above.

The method of dose distribution calculation applicable to the external radiation wherein the therapy is performed by applying radiation of an external X-ray beam or α-ray to the tumor in the patient body is described in detail in the following book: "Computers in Radiotherapy—Physical Aspects," by R. G. Wood. It is one of the series of books issued under the title "Computers in Medicine series" (General Editor: D. W. Hill) in 1974 by the Butterworths Press.

Now, an example of the dose distribution calculation applicable to the external radiation of electron beams will be referred to. Although the contents of the book by R. G. Wood covering the external beam irradiation of X-rays and -rays may be applied in their unmodified form to the external beam irradiation of electron beam, their application has been found to entail inconveniences in accuracy of calculation and application field. Therefore, the present invention performs this external radiation by a different method. This method of calculation is described in detail by the following two dissertations. One of them is the article titled "Betatron Electron Beam Characterization for Dosimetry Calculation" by John D. Stebon, K. Ayyangar, and N. Thuntharalingam and contained in PHYS. MED. BIL., 1979, Vol. 24, No. 2, pages 299-309, (Printed in Great Britain).

This dissertation describes the method for applying the Kawachi's Method to the betatron electron beams as indicated at page 300. The original method of Kawachi is described in detail in the thesis titled "Expedient Calculation Methods of Spatial Dose Distribution of High-Energy Charged Particles," which is Report NIRS-R-6 issued in July, 1977 by National Institute of Radiological Sciences, Anagawa Chiba, Japan. This method is also applicable to the dose calculation of proton rays.

The method for the calculation of dose distribution applicable to the intracavitary therapy or interstitial therapy is specifically described in pages 48 through 63 of the aforementioned book written by R. G. Wood. The contents of Chapter 4 embraces the method of calculation which is applicable to one grain or one rod of radiation source and the method of synthesis of calculations which is applicable to a plurality of irradiation sources inserted or implanted into the patient body. As already touched upon with respect to the embodiment of the dedicated input unit 2, the calculation by this invention can be applied to the intracavitary irradiation by the override type remote afterloading. In the aforementioned book by R. G. Wood, only the non-override method is dealt with in 4.2.3 Programs for Afterloading Devices, in page 59. In the case of the override method, however, the calculation can be easily carried out by regarding one set of three irradiation conditions, i.e. intensity of radiation source, coordinates of position, and radiation time at each override position as radiation conditions for the radiation source.

No calculation of dose can be performed unless the absolute position of the radiation source inserted or implanted into the patient body is known. As already touched upon briefly in the description of the curve digitizer 12 in the section covering the embodiment of FIG. 1, the determination of the absolute position can be materialized by photographing the patient body containing the inserted or implanted radiation source in two mutually perpendicular directions, vertical and horizontal, placing the produced photographic films on the curve digitizer 12, and introducing the data into the micro-processor 1. Besides the photographs taken in the two perpendicular directions, the position of radiation source can be read from the photographic film obtained by stereophotography. In this case, the program for the data input is drawn by a different algorithm.

When the therapy involves combination of the aforementioned external beam irradiation and the intracavitary therapy or interstitial therapy, the calculation of dose distribution is taught in the thesis titled "Advances in the Integration of External Beams and Endocurie Therapy," by F. W. George III et al of University of Southern California, School of Medicine and published in "Proceedings of the Varian Clinac Users Meeting, May 31–June 2, 1978, San Diego, Calif." The present invention follows the contents of this thesis.

As the treatment planning making use of the CT picture images, the present invention adopts the following procedure. As the first step, in the calculation of the dose distribution of the external beam irradiation by the aforementioned radiation technique (such as by means of X-rays or α-rays, the CT images stored in the magnetic tape (MT) are read out by the component 8 of FIG. 1. The question on what type of the CT device has been used for the preparation of MT does not matter. The reading of the CT images from the MT can be effectively obtained so far as the file format of the image data is known. As the second step, the image data thus obtained are copied on the floppy disc through the medium of the floppy disc unit 11. As the result, the MT to be kept in file on the CT device side can be immediately returned and, therefore, prevented from otherwise possible damage or misplacement. There is enjoyed another advantage that the storage of CT images near the apparatus of this invention can be materialized. As the third step, through observation of CT images displayed on the video display 5, the input of command as to the center of the tumor desired to be irradiated, the command as to the gantry angle, etc. is noted from the curve digitizer 12. The therapist, therefore, can learn the anatomical status of the patient body interior and, at the same time, make necessary input of clinical data. As the fourth step, the body contour is automatically extracted by the execution of the program using CT images. As the result, the trouble of feeding figures of body contour one by one through the curve digitizer 12 can be eliminated. As the fifth step, the matrix of electron density is obtained from the data indicating the CT numbers of CT images in the form of matrix and, based on the extracted matrix, calculation for the correction of heterogeneity is performed. As the sixth step, the isodose curves obtained in consequence of the calculation are superposed on the CT images displayed on the screen of the CRT 5, to permit comparison of the detailed CT cross-sectional images of the anatomical status with the dose distribution. Except for the second and third steps of the procedure described above, the first, fourth, fifth and sixth steps are known to the art as disclosed in the theses enumerated below.

(1) "Clinical Application of a CT based-treatment Planning System" by Marc R. Sontag and J. R. Cunningham, Computed Tomography, Vol. 2, pp 117-130, Pergamon Press Ltd. 1978, printed in Great Britain;

(2) "Dosimetric Evaluation of a Computed Tomography Treatment System" by Satish C. Prasad Glenn P. Glasgow and James A. Purdy, Radiology 130: 777-781, March, 1979;

(3) "Potentials of Computed Tomography in Radiation Therapy Treatment Planning" by Edwin C. Mccullough, Radiology 129: 765-768, December, 1978;

(4) "The Equivalent Tisue-Air Ratio Method for Making Absorbed Dose Calculation in Homogeneous Medium" by Marc R. Sontag and John R. Cunningham, Radiology 129: 787-794, December, 1978;

(5) "Computed Tomography Applied to Radiotherapy Treatment Planning: Techniques and Results" by Panline Hobday, Neil Hodson, Janet Husband, Roy P. Parker and James S. Macdonald, Radiology, 133: 477-482, November, 1979;

(6) "Three Dimentioned Model for CT radiotherapy Treatment Planning" by Steven L. Fritz, IEEE 1979. CH 1404-3/79/0000-0061 $0.75; and (7) "An Interactive Treatment Planning Using Computed Tomography for Intracavitary Radiotherapy" by Kyo Rak Lee, William H. Anderson, Sanwell J. Dwyer III, Hollace L. Cox, Cal M. Mansfield, Errol Levine and Arch W. Templeton IEEE 1979 CH1404-3/79/0000-0056 $0.75;

(8) "Localization in Interstitial Dosimetry Utilizing the CT Scanner" by Arnold Herskovic, Thomas N. Padical and Sang N. Lee, Computed Tomography Vol. 3, pp 101 to 103;

(9) "Format Conversion of the Magnetic Tapes for Exchanging the CT Image Information" by Masaomi Takisawa, Toshio Kobayashi; Kiyoshi Maruyama, Kesato Yano, and Eiichi Takenaka.

The titles of the pieces of literature, (1) through (9), enumerated above clearly show which of the methods taught therein are useful for the first, fourth, fifth, and sixth steps of the procedure of the present invention. One of these theses contributes to the materializations of a plurality of measures involved in the first, fourth and fifth steps of the procedure.

For the extraction of the body contour as the fourth step of the procedure, the methods taught in the following pieces of literature have provided useful information.

(10) "Contour Extraction of RI Image" January, 1980 issue of the Video Information (M) (Homma, Shimizu, Takenaka and Nakaya); and

(11) "Heart Contour Extraction of Chest X-ray Image," April, 1980 issue of the Video Information (M) (Hasegawa and Torwaki).

The effects manifested by the method of body contour extraction on the embodiment described above will be briefly summarized. In the first place, in the case of the external radiation, there is brought about a clinically highly advantageous effect because, on the screen of the video monitor 5, the CT images are displayed to show anatomically or morphologically detailed cross sections of the patient body and, at the same time, the isodose curves obtained in consequence of the calculation of dose distribution of the theory that the aforementioned anatomical or morphological images serve as the information for calculation (as by utilizing the results of contour extraction) are superposed. As a synergistic effect, the therapist, by depressing specific pushbutton switches and rotating the dial on the dedicated input unit 2 thereby changing the numerical values of desired parameters of therapeutic conditions, can cause the corresponding isodose curves to be displayed with a slight time lag in the form of a slow motion picture on the video monitor 5. By comparing the isodose curves with the detailed information produced by the CT images, he can accomplish an outstanding clinical effect. For example, he can carry out the realtime fast optimization cycle indicated in FIG. 4 by causing the isodose curves of high dose level of not less than 90 percent to cover as much as possible the tumor discernible from the CT images thereby making as much contribution to the tumor control and, in the meantime, visually confirming that the isodose curves of low dose level of not more than 30 percent cover the healthy tissue discernible from the CT images, particularly the critical organ or organs.

Similar effects can be manifested in the other methods of radiation than the external radiation, such as the intracavitary therapy or interstitial therapy.

As described above, the apparatus for realtime fast reconstruction and display of dose distribution provided by the present invention incorporates a fast reconstructer, a dedicated input unit, a video memory, etc. in addition to the configuration of the conventional apparatus for calculation of dose distribution. The fast reconstructer cyclically performs the calculation of dose distribution for each plane (one frame of picture images) at a high speed and causes the results of the calculation to be displayed on the CRT and, by the rotation of the dial on the dedicated input unit during the repeated cycle, enables the therapeutic conditions to be continuously changed, and causes the results of calculation reflecting such continuous changes of therapeutic conditions to be displayed as isodose curves in the form of a slow motion picture. This apparatus, therefore, offers a salient feature that the therapist is enabled instantaneously to fit the dose distribution optimized for the patient under treatment.

What is claimed is:

1. Apparatus for realtime fast reconstruction and display of dose distribution which calculates the absorbed dose in an irradiated area defined by coordinates and displays the results of the calculation, said apparatus comprising:

input means capable of setting parameters in the form of time-continuous quantities;

a dedicated digital computer serving to control the input by said input means;

dedicated realtime fast reconstruction means for calculating the absorbed dose for each coordinate in the exposed area at a high speed by decomposing calculation formulae necessary for obtaining isodose curves on the basis of the parameter set in said input means and effecting parallel calculation of the decomposed formulae, thereby obtaining the isodose curves; and video display means for storing and displaying the isodose curves classified in terms of different isodose levels;

said calculation being continuously repeated to provide a motion picture of the dose distribution when the magnitude of said parameters is varied.

2. The apparatus according to claim 1 wherein said input means comprises interruption means for stopping said continuously repeated calculation.

3. The apparatus according to claim 1 wherein said dose distribution is superposed by other information for display.

* * * * *

UNITED STATES PATENT AND TRADEMARK OFFICE
CERTIFICATE OF CORRECTION

PATENT NO. : 4,455,609

DATED : 6/19/84

INVENTOR(S) : Inamura et al.

It is certified that error appears in the above-identified patent and that said Letters Patent is hereby corrected as shown below:

| COLUMN | LINE | DESCRIPTION |
|---|---|---|
| 10 | 05 | delete "tyical" insert --typical-- |
| 16 | 03 | delete "x" |
| 16 | 06 | insert --x-- infront of "ocr" |

Signed and Sealed this

Twentieth Day of September, 1988

Attest:

DONALD J. QUIGG

Attesting Officer

Commissioner of Patents and Trademarks